(12) United States Patent
Zaima et al.

(10) Patent No.: US 8,178,716 B2
(45) Date of Patent: May 15, 2012

(54) METHOD OF CRYSTALLIZATION

(75) Inventors: Fumiya Zaima, Okayama (JP); Nirou Hoshishima, Okayama (JP)

(73) Assignees: Mitsubishi Gas Chemical Company, Inc., Tokyo (JP); Toyobo Co., Ltd., Osaka (JP); Mizushima Aroma Company, Ltd., Okayama (JP)

( * ) Notice: Subject to any disclaimer, the term of this patent is extended or adjusted under 35 U.S.C. 154(b) by 321 days.

(21) Appl. No.: 12/299,935

(22) PCT Filed: May 2, 2007

(86) PCT No.: PCT/JP2007/059388
§ 371 (c)(1),
(2), (4) Date: Nov. 7, 2008

(87) PCT Pub. No.: WO2007/129669
PCT Pub. Date: Nov. 15, 2007

(65) Prior Publication Data
US 2009/0182169 A1    Jul. 16, 2009

(30) Foreign Application Priority Data

May 8, 2006 (JP) .................................. 2006-129158

(51) Int. Cl.
*C07C 51/16* (2006.01)
(52) U.S. Cl. ........ 562/417; 562/405; 562/407; 562/408; 562/409; 562/412
(58) Field of Classification Search .......... None
See application file for complete search history.

(56) References Cited

U.S. PATENT DOCUMENTS 3,452,088 A    6/1969    Olsen et al.

FOREIGN PATENT DOCUMENTS

| JP | 07-215914 | 8/1995 |
|----|-----------|--------|
| JP | 11-092415 | 4/1999 |
| JP | 2000-086577 | 3/2000 |
| JP | 2004-216331 | 8/2004 |
| JP | 2004-315456 | 11/2004 |
| JP | 2006-096710 | 4/2006 |
| JP | 2006-143612 | 6/2006 |
| WO | WO 02/098835 A1 | 12/2002 |

*Primary Examiner* — Sudhakar Katakam
(74) *Attorney, Agent, or Firm* — Antonelli, Terry, Stout & Kraus, LLP.

(57) ABSTRACT

The present invention relates to a multi-stage crystallization process which comprises the steps of feeding a solution of terephthalic acid or a slurry (raw slurry) containing terephthalic acid partially precipitated to a first crystallization vessel to precipitate the terephthalic acid therein; and feeding a slurry (crystallization slurry) containing the thus precipitated terephthalic acid sequentially to second and subsequent crystallization vessels, wherein while continuously supplying a cleaning solvent to a delivery conduit connecting the former-stage crystallization vessel and the next latter-stage crystallization vessel to each other, the crystallization slurry is fed through the delivery conduit. There is provided a multi-stage crystallization process using a solution of terephthalic acid or a slurry containing terephthalic acid partially precipitated as a raw material in which even when the process is operated for a period as long as several months, the delivery conduit is free from occurrence of clogging.

9 Claims, No Drawings

METHOD OF CRYSTALLIZATION

TECHNICAL FIELD

The present invention relates to a crystallization process in which a solution of terephthalic acid or a slurry containing terephthalic acid partially precipitated is used as a raw material, and more particularly to a multi-stage crystallization process employing a plurality of crystallization vessels in which a solution of terephthalic acid or a slurry containing terephthalic acid partially precipitated is used as a raw material.

BACKGROUND ART

In general, terephthalic acid is produced by liquid-phase oxidation reaction of p-phenylene group-containing compounds, e.g., p-dialkyl benzenes such as typically p-xylene, and then purified by various methods. The liquid-phase oxidation reaction is usually conducted in an acetic acid solvent in the presence of a catalyst such as cobalt and manganese or the catalyst and a promoter such as a bromine compound and acetaldehyde. As the method of purifying crude terephthalic acid produced by the liquid-phase oxidation reaction, there are known various methods such as the method of dissolving the crude terephthalic acid in acetic acid, water or a mixed solvent thereof under high-temperature and high-pressure conditions and then subjecting the resultant solution to catalytic hydrogenation treatment, decarbonylation treatment, oxidation treatment or recrystallization treatment, and the method of subjecting a slurry containing terephthalic acid crystals partially dissolved therein to a high-temperature immersion treatment.

The terephthalic acid may be purified by combination of a plurality of these treatments. For example, a solution of terephthalic acid or a slurry containing terephthalic acid partially precipitated which has been purified by the catalytic hydrogenation treatment, etc., is further subjected to crystallization treatment to obtain a high-purity terephthalic acid.

In the crystallization treatment, flush evaporation of a solvent may be used in some cases. In this case, a low-pressure and low-temperature slurry obtained by flush evaporation of the solvent is subjected to solid-liquid separation to obtain a high-purity terephthalic acid. In addition, the crystallization treatment may also be conducted by a multistage crystallization method. In this case, a plurality of crystallization vessels may be arranged in series, and connected to each other through a delivery conduit provided with a control valve for controlling a flow rate of the slurry fed therethrough.

In the treatments such as crystallization treatment in which a slurry is handled and treated, it is important to control a solubility of the terephthalic acid. More specifically, in order to improve a yield of the terephthalic acid, it is important to use the conditions in which crystals thereof are readily precipitated. However, on the other hand, it is often undesirable that the crystals are precipitated outside of the crystallization vessels. For this reason, as to the treatment steps in which such a slurry is handled and treated, there are known various techniques for preventing precipitation of the crystals. For example, in JP 2004-315456A, there is disclosed the technique in which a slurry treating apparatus disposed in a crystallization step of a process for producing a high-purity terephthalic acid, is charged with a sealing solution having a temperature ranging from a temperature lower by 30° C. than a slurry temperature in the apparatus (slurry temperature–(minus) 30° C.) to the slurry temperature. In the technique described in JP 2004-315456A, the crystals are prevented form being deposited onto slurry treating equipments which includes meters such as a level meter, a pressure gauge and a flow meter, valves such as a control valve, a stirrer bearing, and a equipments disposed on a slurry withdrawal line such as a pump, etc. Also, in JP 2000-86577A, there is disclosed the process for producing a high-purity terephthalic acid in which the terephthalic acid is crystallized by adding a large amount of low-temperature water to an aqueous solution obtained after a hydrogenation treatment to reduce the temperature of the aqueous solution. In the technique described in JP 2000-86577A, precipitation or deposition of the crystals is prevented, and handling of the crystals upon transportation, etc., can be facilitated.

Especially in the multi-stage crystallization process, it is important to control a solubility of the terephthalic acid, and there is known such a problem that a delivery conduit suffers from clogging owing to deposition of the precipitated terephthalic acid crystals. This is because a high-pressure and high-temperature slurry containing terephthalic acid undergoes decrease in pressure and temperature when flowing through the delivery conduit. The precipitated terephthalic acid crystals are deposited onto an inner wall surface of the delivery conduit, thereby narrowing a flow path of the slurry and finally clogging the flow path.

The above problem concerning clogging of the delivery conduit may be solved by interrupting the crystallization step and cleaning an inside of the delivery conduit. However, this method still has problems concerning a stability of yield or quality of the products. Further, since precipitation of the crystals is caused in the delivery conduit disposed between the crystallization vessels, the method of preventing clogging of the flow path simply by dissolving the terephthalic acid crystals deposited onto the inner wall surface of the delivery conduit tends to reduce a yield of a high-purity terephthalic acid and, therefore, is disadvantageous in view of productivity thereof. Therefore, in order to not only prevent clogging of the delivery conduit but also achieve stable yield or quality of the products, the technique described in JP 2004-315456A which relates to such a technique for preventing precipitation of the crystals at a position other than the delivery conduit, and the technique described in JP 2000-86577A using a large amount of water are both unsatisfactory. Therefore, there is a demand for developing further effective techniques.

DISCLOSURE OF THE INVENTION

An object of the present invention is to provide a multi-stage crystallization process using a solution of terephthalic acid or a slurry containing terephthalic acid partially precipitated as a raw material, which is free from clogging of a delivery conduit connecting crystallization vessels to each other even after the process is continuously operated for a period as long as 2 to 6 months.

The inventors have attempted various methods for preventing clogging of the delivery conduit such as reduction in length of the delivery conduit, heating of the delivery conduit, increase in flow rate of the slurry flowing through the delivery conduit and change in temperature drop pattern of the multi-stage crystallization process. However, any of these methods fails to completely prevent clogging of the delivery conduit.

As a result of further intensive and extensive researches to solve the above problems, the inventors have found that when continuously supplying a cleaning solvent to a delivery conduit connecting respective crystallization vessels to each other, the delivery conduit can be prevented from suffering from clogging by terephthalic acid crystals precipitated in the crystallization step. The present invention has been accomplished on the basis of the above finding.

Thus, the present invention provides a multi-stage crystallization process comprising the steps of:

feeding a solution of terephthalic acid or a slurry (raw slurry) containing terephthalic acid partially precipitated to a first crystallization vessel to precipitate the terephthalic acid therein; and feeding a slurry (crystallization slurry) containing the thus precipitated terephthalic acid sequentially to second and subsequent crystallization vessels, wherein while continuously supplying a cleaning solvent to a delivery conduit connecting the former-stage crystallization vessel and the next latter-stage crystallization vessel to each other, the crystallization slurry is fed through the delivery conduit.

In accordance with the present invention, there is provided a multi-stage crystallization process in which when continuously supplying a cleaning solvent to a delivery conduit connecting two crystallization vessels to each other, it is possible to conduct a continuous stable operation without clogging of the delivery conduit, and enhance a stability of yield or quality of a high-purity terephthalic acid.

PREFERRED EMBODIMENTS FOR CARRYING OUT THE INVENTION

The present invention is described in detail below.

The present invention relates to a process for crystallization of terephthalic acid using a multi-stage crystallization method which is suitably applied to a purification step upon producing a high-purity terephthalic acid from a crude terephthalic acid, and is characterized by the method of delivering a slurry containing a terephthalic acid between crystallization vessels.

The crude terephthalic acid may be produced by conventionally known methods, for example, by a liquid-phase oxidation reaction of p-phenylene group-containing compounds, e.g., p-dialkyl benzenes such as typically p-xylene.

The crystallization process of the present invention is applied to a purification step upon producing a high-purity terephthalic acid from the crude terephthalic acid as described above. In the purification step, conventionally known purification methods are preferably used in combination of any two or more thereof. Thus, the crystallization process of the present invention is applied to a solution of terephthalic acid or a slurry containing terephthalic acid partially precipitated (in the present specification, the "slurry" is occasionally referred to as a "raw slurry") which are purified by the conventionally known purification methods. The conventionally known purification methods include, for example, the method of dissolving the crude terephthalic acid in acetic acid, water or a mixed solvent thereof under high-temperature and high-pressure conditions and then subjecting the resultant solution to catalytic hydrogenation treatment, decarbonylation treatment, oxidation treatment or recrystallization treatment, the method of subjecting a slurry containing terephthalic acid crystals partially dissolved therein to high-temperature immersion treatment, etc. Among these purification methods, preferred are those methods using a catalytic hydrogenation treatment from the standpoints of purification efficiency and a stable quality of the resultant high-purity terephthalic acid. The catalytic hydrogenation treatment is usually conducted by dissolving the crude terephthalic acid in water and then subjecting the obtained aqueous solution to catalytic hydrogenation reaction. By conducting the catalytic hydrogenation treatment, a solution of terephthalic acid having a temperature of from about 270° C. to about 300° C. is produced.

The crystallization process of the present invention is a multi-stage crystallization process in which a high-pressure and high-temperature solution or raw slurry of terephthalic acid is crystallized in a multi-stage manner using 2 to 6 crystallization vessels arranged in series. In order to crystallize the terephthalic acid in the respective crystallization vessels, there may be used the method of cooling the solution or raw slurry by flush evaporation of a solvent contained therein. In the first crystallization vessel (which means a crystallization vessel into which the solution or raw slurry of terephthalic acid is charged), the terephthalic acid is crystallized by such a cooling method, thereby producing a slurry containing the thus crystallized terephthalic acid (in the present specification, the "slurry" is referred to as a "crystallization slurry" to distinguish it from the raw slurry).

The crystallization vessels are connected with each other through a delivery conduit, so that the crystallization slurry continuously flows from the former-stage crystallization vessel to the next latter-stage crystallization vessel through the delivery conduit. The delivery conduit is preferably fitted with a control valve for controlling a flow rate of the crystallization slurry flowing therethrough. The control valve is preferably operated such that an opening degree thereof is determined according to an operation output signal generated on the basis of feed back control from a controller, thereby controlling a flow rate of the crystallization slurry flowing through the delivery conduit. The feed back control is not particularly limited. For example, PID control may be usually used as the feed back control. The PID control used herein means such a control in which the opening degree of the control valve as an object to be controlled approaches a target value by using control variables including P (proportional action), I (integral action) and D (derivative action). Also, the controller for controlling the control valve is preferably a level meter provided in the former-stage crystallization vessel.

In the multi-stage crystallization process, in general, the first crystallization vessel is kept at a highest temperature and a highest pressure, and the temperature and the pressure of the respective crystallization vessels both are decreased in the order of the second and third crystallization vessels (the second and third crystallization vessels mean those vessels located at the second position and the third position, respectively, when they are arranged in series). Therefore, the inside temperature and the inside pressure of the delivery conduit connecting the two adjacent crystallization vessels is not uniform over a whole length thereof, and both of the temperature and pressure within the delivery conduit are decreased as the position in the delivery conduit approaches the next latter-stage crystallization vessel.

Hitherto, if the crystallization slurry is delivered through such a delivery conduit having such a gradient of the temperature and the pressure, additional terephthalic acid crystals tend to be precipitated within the delivery conduit owing to the decrease in temperature and pressure, and deposited onto an inner wall surface of the delivery conduit.

In the present invention, by continuously supplying a cleaning solvent into the delivery conduit, the amount of the terephthalic acid crystals deposited can be reduced, and the terephthalic acid crystals, if deposited, can be dissolved and separated therefrom.

In the present invention, the condition between the first and second crystallization vessels is as follows. That is, in the continuous multi-stage crystallization process of the present invention, the solution of terephthalic acid or the slurry containing terephthalic acid partially precipitated is fed to the former-stage crystallization vessel to precipitate the terephthalic acid therein, thereby producing a slurry containing the precipitated terephthalic acid and a solvent, and then the thus produced slurry is fed to the next latter-stage crystallization vessel, wherein while continuously supplying a cleaning solvent to the delivery conduit connecting the former-stage crystallization vessel and the next latter-stage crystallization vessel with each other, the slurry containing the precipitated terephthalic acid and the solvent is fed through the delivery conduit.

For the purpose of reducing the amount of the cleaning solvent used, the cleaning solvent may be fed intermittently. When being fed intermittently, the cleaning solvent may be supplied for a period of from 10 s to 1 h at intervals of from 10 min to 12 h and preferably for a period of from 15 s to 20 min at intervals of from 10 min to 6 h.

The cleaning solvent preferably has the same composition as that of the solvent contained in the crystallization slurry flowing through the delivery conduit. As the cleaning solvent, water may be suitably used.

The temperature of the cleaning solvent is preferably not higher than a temperature of the former-stage crystallization vessel but not lower than a temperature of the next latter-stage crystallization vessel and more preferably not higher than the temperature of the former-stage crystallization vessel but not lower than a temperature higher by 5° C. than the temperature of the next latter-stage crystallization vessel (temperature of the next latter-stage crystallization vessel+(plus) 5° C.). When the temperature of the cleaning solvent lies within the above-specified range, the terephthalic acid can be prevented from being deposited within the delivery conduit, and the effect of dissolving the deposited terephthalic acid can be attained, and further deterioration in yield of the terephthalic acid can be prevented.

The amount of the cleaning solvent supplied is preferably from 0.5 to 15% by weight, more preferably from 0.5 to 10% by weight and still more preferably from 1 to 8% by weight on the basis of the amount (on a weight basis) of the crystallization slurry flowing through the delivery conduit.

The cleaning solvent is supplied into the delivery conduit from a cleaning nozzle disposed in a horizontal direction of the delivery conduit and mixed in the crystallization slurry. The cleaning solvent may be supplied at only one position of the delivery conduit, but is preferably supplied at a plurality of positions of the delivery conduit. In the latter case, the cleaning solvent is preferably supplied at one position per 0.3 to 1.5 m of a length of the delivery conduit. When the cleaning solvent is fed at a plurality of positions of the delivery conduit, an excellent effect of separating the terephthalic acid crystals deposited on the inner wall surface of the delivery conduit can be attained, so that the delivery conduit can be prevented from suffering from clogging over a broad region of an inner surface thereof. The control valve is preferably disposed on the delivery conduit at its portion very close to the latter-stage crystallization vessel. Therefore, the cleaning nozzle is usually disposed at such a position of the delivery conduit between the former-stage crystallization vessel and the control valve.

The cleaning solvent is preferably supplied at a constant angle $\phi$ relative to the direction of a flow of the crystallization slurry fed through the delivery conduit from an upstream side to a downstream side thereof (angle $\phi$ means an angle between the flowing direction of the crystallization slurry and the feeding direction of the cleaning solvent). When the angle $\phi$ is kept constant, the cleaning solvent can be suitably supplied into the delivery conduit without disturbing the flow of the crystallization slurry within the delivery conduit to a more than necessary extent. The angle $\phi$ is preferably from 30 to 60° and more preferably from 35 to 55°.

The cleaning nozzle used for supplying the cleaning solvent into the delivery conduit is preferably provided with a throttled feed orifice at its position very close to the delivery conduit in order to effectively increase a linear feed velocity of the cleaning solvent. For the purpose of mainly re-dissolving the terephthalic acid crystals deposited on the inner wall surface of the delivery conduit, the linear feed velocity of the cleaning solvent is preferably from 10 to 120 [m/s]. Also, for the purpose of mainly separating the terephthalic acid crystals deposited on the inner wall surface of the delivery conduit, the linear feed velocity of the cleaning solvent is preferably from 15 to 200 [m/s] and more preferably from 40 to 200 [m/s].

Examples of a material of the delivery conduit include those generally used in a purification step of a process for producing a high-purity terephthalic acid, such as a stainless steel material, a Hastelloy material and a titanium material. Among these materials, preferred is the titanium material capable of forming a smooth hard surface having a strong anti-corrosion property, since the terephthalic acid crystals are hardly deposited thereon under the conditions upon use.

The content of the terephthalic acid in the crystallization slurry flowing through the delivery conduit connecting the crystallization vessels with each other, may be determined according to amount of the crude terephthalic acid mixed in the purification step, temperature of the catalytic hydrogenation reaction, multi-stage crystallization conditions (such as number of crystallization stages, crystallization temperature patterns and amount of the solvent flushed in the respective crystallization vessels), etc. The content of the terephthalic acid in the crystallization slurry is preferably from 5.0 to 45.0% by weight and more preferably from 10.0 to 37.0% by weight.

The flow rate of the crystallization slurry flowing through the delivery conduit connecting the crystallization vessels with each other may be adjusted so as not to cause precipitation of the terephthalic acid crystals within the delivery conduit, and is preferably from 0.5 to 4.0 [m/s] and more preferably from 0.7 to 3.0 [m/s].

The length of the delivery conduit connecting the crystallization vessels with each other is preferably as short as possible from the standpoint of avoiding clogging thereof. However, it is not possible to extremely reduce a length of the delivery conduit, owing to limitations to installation space of the crystallization vessels within the plant. The length of the delivery conduit is preferably from 1.0 to 15.0 m and more preferably from 2.0 to 10.0 m.

EXAMPLES

The present invention is described in more detail by referring to the following examples. However, it should be noted that these examples are only illustrative and not intended to limit the invention thereto.

Example 1

Using a commercial scale high-purity terephthalic acid production apparatus, crude terephthalic acid was produced by a liquid-phase oxidation method. In the purification step, the crude terephthalic acid obtained by the liquid-phase oxidation method was subjected to catalytic hydrogenation reaction at 281° C., and the terephthalic acid solution as the resultant reaction solution was fed to the first crystallization vessel where water as a solvent was evaporated by flush evaporation to produce a crystallization slurry having a temperature of about 250° C. The thus obtained crystallization slurry having a temperature of about 250° C. was continuously fed to the second crystallization vessel maintained at about 220° C. through a delivery conduit (made of titanium and having a length of 6.5 m) fitted with a control valve at a flow rate of 127.0 tons per hour (content of terephthalic acid in the slurry: 27.4% by weight). At this time, hot water heated to 235° C. was continuously supplied into the delivery conduit from five cleaning nozzles at a flow rate of 5.1 tons per hour (4.0% by weight of the flow rate of the crystallization slurry).

(Linear feed velocity of the cleaning solvent at a feed orifice of each cleaning nozzle: 110 [m/s]; feed angle of the cleaning solvent: 450; flow rate of the slurry: 2.5 [m/s])

As a result, it was confirmed that the process was able to be continuously operated for 4 months in a stable manner without occurrence of clogging of the delivery conduit.

Example 2

The same operational procedure as in Example 1 was repeated except that hot water heated to 230° C. was supplied at a flow rate of 9.2 tons per hour (7.3% by weight of the flow rate of the slurry; linear feed velocity of the cleaning solvent at a feed orifice of each cleaning nozzle: 199 [m/s]). As a result, it was confirmed that the process was able to be continuously operated for 6 months in a stable manner without occurrence of clogging of the delivery conduit.

Example 3

The same operational procedure as in Example 1 was repeated except for using a delivery conduit made of stainless steel. As a result, it was confirmed that the process was able to be continuously operated for 3 months in a stable manner without occurrence of clogging of the delivery conduit.

Example 4

The same operational procedure as in Example 1 was repeated except for using 10 cleaning nozzles (linear feed velocity of the cleaning solvent at a feed orifice of each cleaning nozzle: 55 [m/s]). As a result, it was confirmed that the process was able to be continuously operated for 5 months in a stable manner without occurrence of clogging of the delivery conduit.

Example 5

The same operational procedure as in Example 1 was repeated except that hot water heated to 230° C. was supplied at a flow rate of 2.5 tons per hour (2.0% by weight of the flow rate of the slurry; linear feed velocity of the cleaning solvent at a feed orifice of each cleaning nozzle: 55 [m/s]). As a result, it was confirmed that the process was able to be continuously operated for 4 months in a stable manner without occurrence of clogging of the delivery conduit.

Example 6

The same operational procedure as in Example 1 was repeated except for using only one cleaning nozzle (linear feed velocity of the cleaning solvent at a feed orifice of cleaning nozzle: 138 [m/s]). As a result, it was confirmed that the process was able to be continuously operated for 2 months in a stable manner without occurrence of clogging of the delivery conduit.

Example 7

The same operational procedure as in Example 1 was repeated except that the linear feed velocity of the cleaning solvent at a feed orifice of each cleaning nozzle was changed to 18 [m/s]. As a result, it was confirmed that the process was able to be continuously operated for 2 months in a stable manner without occurrence of clogging of the delivery conduit.

Comparative Example 1

The same operational procedure as in Example 1 was repeated except for feeding no cleaning solvent and using a delivery conduit made of stainless steel. As a result, it was confirmed that when operated for 5 days, the delivery conduit suffered from clogging.

Comparative Example 2

The same operational procedure as in Example 1 was repeated except for feeding no cleaning solvent. As a result, it was confirmed that when operated for 7 days, the delivery conduit suffered from clogging.

INDUSTRIAL APPLICABILITY

In accordance with the present invention, there is provided a multi-stage crystallization process which can be continuously operated in a stable manner without clogging of a delivery conduit connecting two crystallization vessels with each other, and is capable of enhancing a stability of yield or quality of a high-purity terephthalic acid produced.

The invention claimed is:
1. A multi-stage crystallization process comprising the steps of:
  feeding a solution of terephthalic acid or a slurry (raw slurry) containing terephthalic acid partially precipitated to a first crystallization vessel to precipitate the terephthalic acid therein; and
  feeding a slurry (crystallization slurry) containing the thus precipitated terephthalic acid sequentially to at least a second crystallization vessel,
  wherein a solvent contained in the crystallization slurry is water, and while continuously supplying water as a cleaning solvent to a delivery conduit connecting the former-stage crystallization vessel and the next latter-stage crystallization vessel to each other, the crystallization slurry is fed through the delivery conduit, and
  wherein the cleaning solvent is supplied to the delivery conduit at an angle of 30 to 60° relative to a direction of a flow of the crystallization slurry fed through the delivery conduit from an upstream side to a downstream side thereof by means of a cleaning nozzle, and a linear feed velocity of the cleaning solvent at a feed orifice of the cleaning nozzle is from 15 to 200 [m/s].
2. The crystallization process according to claim 1, wherein the terephthalic acid is precipitated in the respective crystallization vessels by a cooling method using flush evaporation of a solvent contained in the solution or slurry.
3. The crystallization process according to claim 1, wherein a temperature of the cleaning solvent is not higher than a temperature of the former-stage crystallization vessel but not lower than a temperature of the next latter-stage crystallization vessel.

4. The crystallization process according to claim 1, wherein a flow rate of the cleaning solvent supplied is from 0.5 to 15% by weight of a flow rate of the crystallization slurry flowing through the delivery conduit.

5. The crystallization process according to claim 1, wherein the cleaning solvent is supplied to the delivery conduit at one position per 0.3 to 1.5 m of a length of the delivery conduit.

6. The crystallization process according to claim 1, wherein the delivery conduit is made of a titanium material.

7. The crystallization process according to claim 1, wherein a total number of the crystallization vessels in series is 2-6.

8. The crystallization process according to claim 1, wherein both a temperature and pressure within the delivery conduit decreases as the position in the delivery conduit approaches the next latter-stage crystallization vessel.

9. The crystallization process according to claim 1, wherein the slurry (crystallization slurry) containing the thus precipitated terephthalic acid is sequentially fed to second and subsequent crystallization vessels.

* * * * *